(12) United States Patent
Wald et al.

(10) Patent No.: US 11,096,605 B2
(45) Date of Patent: Aug. 24, 2021

(54) MODULAR COIL ASSEMBLY

(71) Applicant: Medtronic Navigation, Inc., Louisville, CO (US)

(72) Inventors: Andrew Wald, Denver, CO (US); Brad Jacobsen, Erie, CO (US); Danail G. Danailov, Westminster, CO (US); Steven L. Hartmann, Superior, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 860 days.

(21) Appl. No.: 14/673,994

(22) Filed: Mar. 31, 2015

(65) Prior Publication Data

US 2016/0287132 A1 Oct. 6, 2016

(51) Int. Cl.
*A61B 5/06* (2006.01)
*A61B 34/20* (2016.01)
*H01F 5/02* (2006.01)
*H01F 41/04* (2006.01)

(52) U.S. Cl.
CPC .............. *A61B 5/062* (2013.01); *A61B 34/20* (2016.02); *H01F 5/02* (2013.01); *H01F 41/04* (2013.01); *A61B 2034/2051* (2016.02); *A61B 2034/2068* (2016.02); *A61B 2034/2072* (2016.02); *A61B 2562/12* (2013.01); *H01F 2005/027* (2013.01)

(58) Field of Classification Search
CPC combination set(s) only.
See application file for complete search history.

(56) References Cited

U.S. PATENT DOCUMENTS

| 3,800,213 | A | | 3/1974 | Rorden |
| 4,103,197 | A | | 7/1978 | Ikegami et al. |
| 5,281,941 | A | | 1/1994 | Bernstein |
| 5,425,367 | A | | 6/1995 | Shapiro et al. |
| 5,552,008 | A | * | 9/1996 | Hecht ..................... C04B 35/83 |
| | | | | 156/174 |
| 5,645,065 | A | | 7/1997 | Shapiro et al. |
| 5,672,967 | A | | 9/1997 | Jensen et al. |
| 5,913,820 | A | | 6/1999 | Bladen et al. |

(Continued)

FOREIGN PATENT DOCUMENTS

| DE | 3433003 A1 | 3/1986 | |
| DE | 10162693 C1 * | 3/2003 | ............... H01F 5/02 |

(Continued)

OTHER PUBLICATIONS

International Search Report and Written Opinion dated Jun. 16, 2016 for PCT/US2016/023872 which claims the benefit of U.S. Appl. No. 14/673,994, filed Mar. 24, 2016.

(Continued)

*Primary Examiner* — Yi-Shan Yang
(74) *Attorney, Agent, or Firm* — Harness, Dickey & Pierce, P.L.C.

(57) ABSTRACT

In various specific embodiments, a localizer can include a plurality of coil groups, where each coil group includes three coils that are formed around a single center. Each of the three coils can be formed around separate jigs and the jigs can be interconnected to form the coil group. The jigs need not be annular, but may be formed in any appropriate configuration of shape or geometry for forming the final coil group.

22 Claims, 8 Drawing Sheets

(56) References Cited

U.S. PATENT DOCUMENTS

| | | |
|---|---|---|
| 5,963,120 A | 10/1999 | Zaviska |
| 6,061,644 A | 5/2000 | Leis |
| 6,134,420 A | 10/2000 | Flowerdew et al. |
| 6,144,119 A | 11/2000 | Hazelton |
| 6,204,823 B1 | 3/2001 | Spano et al. |
| 6,373,364 B1 | 4/2002 | Son et al. |
| 6,374,134 B1 | 4/2002 | Bladen et al. |
| 6,380,732 B1 | 4/2002 | Gilboa |
| 6,611,141 B1 | 8/2003 | Schulz et al. |
| 6,822,570 B2 | 11/2004 | Dimmer et al. |
| 6,865,799 B2 | 3/2005 | Hata et al. |
| 6,977,504 B2 | 12/2005 | Wright et al. |
| 7,011,266 B2 | 3/2006 | Hashimoto et al. |
| 7,026,927 B2 | 4/2006 | Wright et al. |
| 7,161,451 B2 | 1/2007 | Shen |
| 7,193,578 B1 | 3/2007 | Harris et al. |
| 7,573,258 B2 | 8/2009 | Anderson |
| 7,658,196 B2 | 2/2010 | Ferreri et al. |
| 7,684,849 B2 | 3/2010 | Wright et al. |
| 7,782,046 B2 | 8/2010 | Anderson |
| 7,809,421 B1 | 10/2010 | Govari |
| 7,816,915 B2 | 10/2010 | Susel et al. |
| 7,911,202 B2 | 3/2011 | Anderson |
| 7,924,000 B2 | 4/2011 | Susel et al. |
| 8,301,226 B2 | 10/2012 | Csavoy et al. |
| 8,350,663 B1 | 1/2013 | Michael |
| 8,452,375 B2 | 5/2013 | Krag et al. |
| 8,467,852 B2 | 6/2013 | Csavoy et al. |
| 8,644,907 B2 | 2/2014 | Hartmann et al. |
| 8,669,763 B2 | 3/2014 | Takatsuji |
| 9,632,201 B2 | 4/2017 | Knizhnik |
| 2001/0020684 A1 | 9/2001 | Hazelton |
| 2001/0022547 A1 | 9/2001 | Murata et al. |
| 2002/0149270 A1 | 10/2002 | Hazelton |
| 2002/0193685 A1 | 12/2002 | Mate et al. |
| 2003/0052785 A1 | 3/2003 | Gisselberg et al. |
| 2003/0192557 A1 | 10/2003 | Krag et al. |
| 2004/0125916 A1 | 7/2004 | Herron et al. |
| 2004/0133101 A1 | 7/2004 | Mate et al. |
| 2004/0138555 A1 | 7/2004 | Krag et al. |
| 2004/0158146 A1 | 8/2004 | Mate et al. |
| 2005/0083242 A1 | 4/2005 | Yagi et al. |
| 2005/0229914 A1 | 10/2005 | Umahashi et al. |
| 2005/0242680 A1 | 11/2005 | Militello et al. |
| 2005/0261570 A1 | 11/2005 | Mate et al. |
| 2006/0106292 A1 | 5/2006 | Anderson |
| 2006/0166681 A1 | 7/2006 | Lohbihler |
| 2007/0120223 A1 | 5/2007 | McKinzie et al. |
| 2007/0129629 A1 | 6/2007 | Beauregard et al. |
| 2007/0157828 A1 | 7/2007 | Susel et al. |
| 2008/0103596 A1 | 5/2008 | Shikinami et al. |
| 2008/0132909 A1 | 6/2008 | Jascob et al. |
| 2008/0238413 A1 | 10/2008 | Anderson |
| 2009/0027149 A1 | 1/2009 | Kocijan |
| 2009/0112128 A1 | 4/2009 | Schiff et al. |
| 2009/0216113 A1 | 8/2009 | Meier et al. |
| 2009/0299174 A1 | 12/2009 | Wright et al. |
| 2010/0160771 A1 | 6/2010 | Gielen et al. |
| 2010/0305427 A1 | 12/2010 | Huber et al. |
| 2010/0321015 A1 | 12/2010 | Susel et al. |
| 2011/0241665 A1 | 10/2011 | Takatsuji |
| 2012/0046542 A1 | 2/2012 | Csavoy et al. |
| 2012/0059389 A1* | 3/2012 | Larson .................. A61N 1/3785 606/129 |
| 2014/0051983 A1 | 2/2014 | Schroeder et al. |
| 2014/0303489 A1 | 10/2014 | Meier et al. |
| 2014/0323852 A1 | 10/2014 | Wald et al. |
| 2014/0339935 A1* | 11/2014 | Harada .................. H02K 3/345 310/71 |
| 2017/0042621 A1 | 2/2017 | Wald et al. |

FOREIGN PATENT DOCUMENTS

| | | | |
|---|---|---|---|
| DE | 10162693 C1 | 3/2003 | |
| EP | 0122133 A1 | 10/1984 | |
| EP | 1174082 A1 * | 1/2002 | ............... A61B 5/06 |
| EP | 1174082 A1 | 1/2002 | |
| EP | 1481637 A1 | 12/2004 | |
| EP | 1806756 A2 | 7/2007 | |
| GB | 369735 A | 3/1932 | |
| JP | 2002107107 A | 4/2002 | |
| JP | 2007184618 A | 7/2007 | |
| JP | 2007-236937 A | 9/2007 | |
| JP | 2008-062040 A | 3/2008 | |
| JP | 2008-188427 A | 8/2008 | |
| JP | WO 2012098851 A1 * | 7/2012 | ............ B60L 11/182 |
| KR | 10-2002-0008775 A | 1/2002 | |
| KR | 10-2007-0074485 A | 7/2007 | |
| WO | WO-2004073283 A2 | 8/2004 | |
| WO | WO-2011020389 A1 | 2/2011 | |
| WO | WO-2011136998 A1 | 11/2011 | |
| WO | WO-2012098851 A1 | 7/2012 | |

OTHER PUBLICATIONS

Japanese Office Action dated Dec. 20, 2016 for Japanese Application No. 2016-510699 corresponding to PCT/US2014/034120 claiming benefit of U.S. Appl. No. 13/871,625, filed Apr. 26, 2013.

International Search Report and Written Opinion dated Aug. 18, 2014 for PCT/US2014/034120 claiming benefit of U.S. Appl. No. 13/871,625, filed Apr. 26, 2013.

International Preliminary Report on Patentability dated Nov. 5, 2015 for PCT/US2014/034120 claiming benefit of U.S. Appl. No. 13/871,625, filed Apr. 26, 2013.

European Office Action dated Nov. 22, 2017 in corresponding/related European Application No. 14726264.6.

Chinese Office Action dated Dec. 28, 2017 in corresponding/related Chinese Application No. 201480023471.2.

International Preliminary Report on Patentability dated Oct. 12, 2017 in corresponding International Application No. PCT/US2016/023872.

Office Action dated Jun. 1, 2018 in corresponding/related Chinese Application No. 201480023471.2.

Australian Office Action dated Aug. 3, 2018 in corresponding/related Australian Application No. 2014257392.

European Office Action dated Sep. 25, 2018 in corresponding/related European Application No. 14726264.6.

European Office Action dated Oct. 17, 2019 in corresponding/related European Application No. 16715201.6.

Japanese Office Action dated Dec. 20, 2016 for Japanese Application No. 2016-510699 corresponding to PCT/US2014/034120 claiming benefit of U.S. Appl. No. 13/871,625, filed Apr. 26, 2013 with English translation.

Office Action dated Oct. 11, 2019 in corresponding/related European Application No. 14726264.6.

Examination Report dated May 1, 2020 in corresponding/related Australian Application No. 2019264657.

Office Action dated Jun. 23, 2020 in corresponding/related European Application No. 16715201.6.

Office Action regarding Korean Patent Application No. 10-2015-7032033, dated Feb. 15, 2021.

* cited by examiner

MODULAR COIL ASSEMBLY

FIELD

The subject disclosure relates to a system for forming a structure, and particularly to a structure for forming a coil.

BACKGROUND

This section provides background information related to the present disclosure which is not necessarily prior art.

A system for determining a location of a tracking device can include a localizer that is configured to emit or generate an electromagnetic field. The electromagnetic field may be sensed by the tracking device and a location of the tracking device may be determined based upon the sensed electromagnetic field. The electromagnetic field may vary over a volume and this variance can be used to determine the location of the tracking device. The localizer device may be formed to include a coil of wire to generate the electromagnetic field once a current is driven through the coil of wire. Forming the localizer array, however, may require several forming and processing steps.

SUMMARY

This section provides a general summary of the disclosure, and is not a comprehensive disclosure of its full scope or all of its features.

A localizer can be formed to generate an electromagnetic field for use in a tracking system that may track a device for a navigation system. That navigation system may include a surgical navigation system to be used with computer-aided surgery. The navigation system may be used to navigate an instrument during a procedure. The localizer can be formed as a transmitter array to include one or a plurality of coils in a specified design.

The coils can be formed to have a common center, but each coil being formed to emit a field having a selected shape and/or intensity. Including a plurality of coils can increase the diversity of the field for increasing possible sensitivity for determining the location of a tracking device. It is understood, however, that a plurality of coils may be placed in a coil array where none or less than all share a center. For example, a coil may be formed on a jig and laid flat with other coils placed adjacent to it, but not including a common center.

In various specific embodiments, a coil array can include a plurality of coil groups, where each coil group includes three coils that are formed around a single center. Each of the three coils can be substantially orthogonal to one another in a final assembly. Each of the three coils can be formed around separate jigs and the jigs can be interconnected to form the coil group. It is understood, however, that the coil group need not share a center and the coil group need not be orthogonal to one another. The jigs need not be annular, but may be formed in any appropriate configuration of shape or geometry for forming the final coil group. Generally, each of the coils of wire can be formed in a jig that is formed with a selected shape.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

A localizer of an electromagnetic (EM) navigation system may include a transmit coil array (TCA). Although the localizers referred to and/or disclosed herein are primarily described as including TCAs (or coil arrays) for transmitting signals (such as emitting or generating an electromagnetic field), the TCAs may be used for receiving signals. The TCA can include multiple sets or groups of coils of conductive material (e.g. wire) for generating the electromagnetic field and may be generally referred to as electromagnetic (EM) coils. Each set of the EM coils may include three orthogonally positioned coils that are used to generate EM fields. Other arrangements are envisioned within the scope of the subject disclosure. Orthogonally positioned coils have respective center axes that are at right angles relative to each other. Also, the axis of all of the coils may intersect at only one point. EM navigation may be enhanced and or performed after a precise and lengthy calibration process for calibrating the TCA. The calibration process can also cause a "bottleneck" in a manufacturing process of a navigation system.

Figure 1:
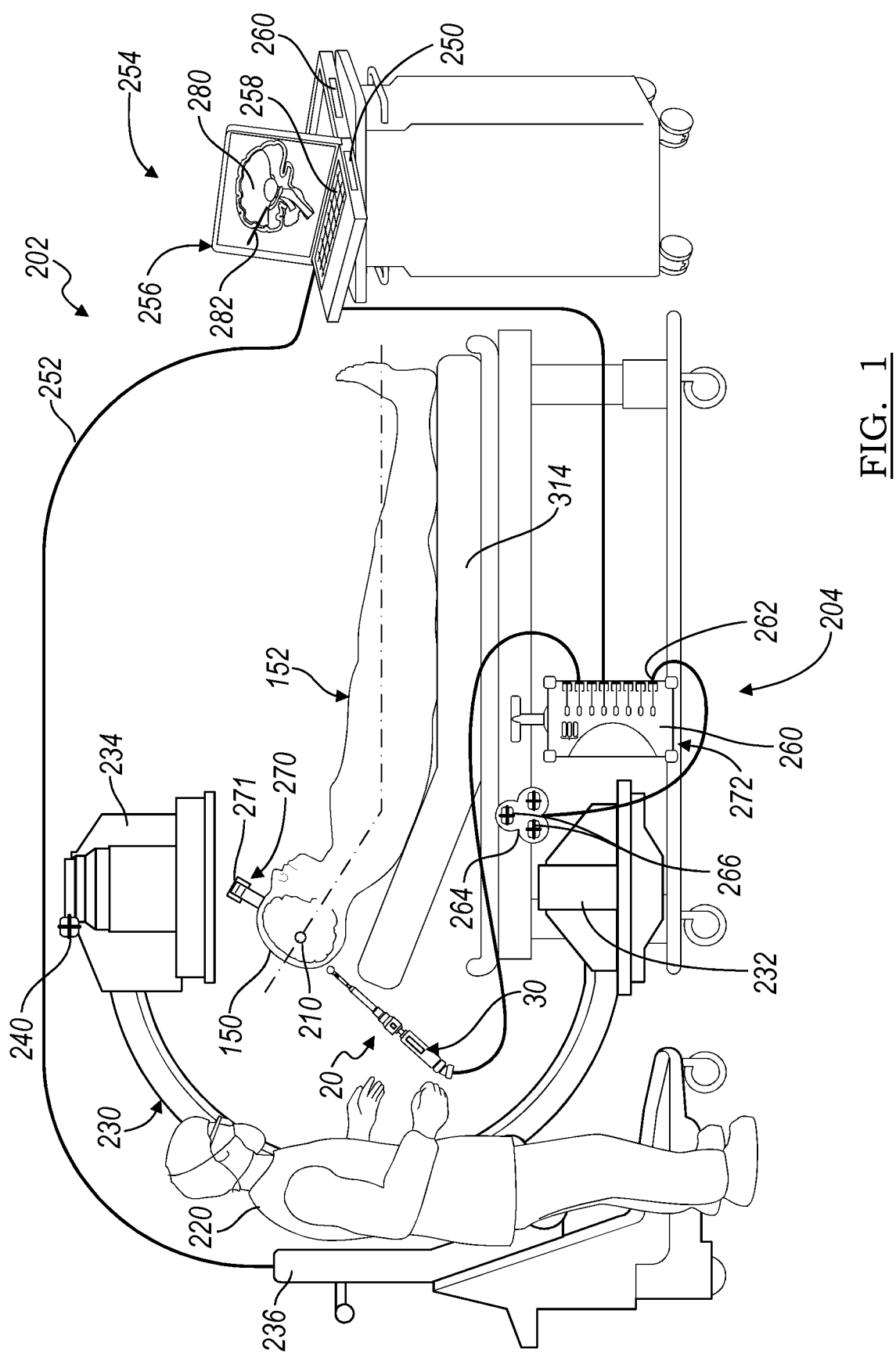
FIG. 1 is a view of a navigation and imaging system.

The calibration process is primarily performed due to inconsistencies, irregularities, and variances between different TCAs. This includes differences in coil placements, number of windings of each coil, lengths of coil wires, sizes of coils, spacing between coils, etc. The differences between coils in the TCA's generally leads to the fields produced by different TCAs to be different. Generally, calibration, therefore, may include factory or prior to use calibration. The calibration may include determining the field or mapping the field produced by each produced TCA, due to manufacturing variances of the coils, to determine the field strengths at different locations relative to the TCA. Accordingly, coil groups, formed as discussed below, may include a variance in field produced from one coil to another that is small or within an error of a navigation system so as to be imperceptible difference (as measured during a calibration process) relative another coil portion or group produced in the same manner. Thus, calibration may be reduced or eliminated. The following disclosed implementations provide TCAs that can lessen calibration processes of TCAs and/or eliminate the need for calibrating TCAs. An example EM navigation system 202 is shown in FIG. 1. The EM navigation system 202 may include any of the TCAs, including the coils discussed therewith, shown and/or described herein. It is understood that the formation of various components, including jigs or windings, as discussed herein may include those disclosed in U.S. Pat. App. Pub. No. 2014/0323852, incorporated herein by reference. For example, additive manufacturing or "3D" printing may be used to form jigs for TCAs, as discussed herein.

Although the EM navigation system 202 is primarily described with respect to performing a procedure on a human patient, the EM navigation system 202 may be used to perform a procedure on other animate and/or inanimate subjects. Also, the implementations disclosed herein may be applied to other EM systems and for purposes other than for position tracking of devices. For example, the implementations may be used to generate EM fields in a transcranial magnetic stimulation system. Also, procedures disclosed herein can be performed relative to a volume, a mechanical device, and/or an enclosed structure. The volume may be of an animate or inanimate object. The subject can be an object that includes an enclosed mechanical device.

With reference to FIG. 1, an instrument assembly may include an appropriate tool or instrument, such as one including a handle or motor and a toolbit. The instrument 20 may include a portion that is positioned relative to, such as within, a skull 150 of a subject 152. The tool assembly 20 may include a tracking device 30 and may be a navigated instrument. As discussed above, the instrument 20 is merely exemplary, and other navigated instruments may include catheters, leads, stimulators, etc. Also, the tracking device 30 may be incorporated into a separate element, such as a removable stylet. The stylet may be placed within a lumen of a catheter.

The tracking device 30 may be interconnected with the navigation system 202. The navigation system 202, as discussed further herein, may include a tracking system 204 that can track the tracking device 30 in six degrees of freedom, including three-dimensional space including a X, Y, Z location and various orientations to determine a position of the tracking device 30 in space. As illustrated above, the instrument 20 may include the tracking device 30 that allows for directly tracking the tool 20 during an implantation and positioning of tool 20. Appropriate tracking devices can include tracking devices as disclosed in U.S. Pat. No. 8,644,907, incorporated herein by reference. Additionally, the navigation system can include the navigation system disclosed in U.S. Patent Application Publication 2014/0323852, incorporated herein by reference.

With continuing reference to FIG. 1, the tool 20 may be used to form an opening or bore 210 in the skull 150 of the subject 152. The bore 210 may be a burr hole formed through the skull 150 as generally understood in the art. The tool 20 may be tracked either directly via the tracking device 30 or via the tracking device on a stylet or other portion associated with the tool 20. Further, as noted above, the tracking device 30 may be associated directly with the tool tip or with another portion of the tool assembly 20. Thus, any one or more of these may be used to track the selected portion of the tool assembly 20.

The navigation of the tool assembly 20 relative to the subject 152 may proceed according to various navigation procedures and techniques, such as those generally known in the art and discussed below, to ensure or assist in positioning the catheter 10 in a selected, including a predetermined or preselected location, within the subject 152. Further, although the following description is related generally to positioning the tool assembly 20 relative to the skull 150 of the subject 152, other navigated procedures may be performed.

The navigation system 202, which may include an electromagnetic navigation system, is primarily described with respect to performing a procedure on a human patient, the navigation system 202 may be used to perform a procedure on other animate and/or inanimate subjects, including those navigation systems as disclosed in U.S. Pat. App. Pub. No. 2014/0323852, incorporated herein by reference. Also, procedures disclosed herein can be performed relative to a volume, a mechanical device, and/or an enclosed structure. The volume may be of an animate or inanimate object. The subject can be an object that includes an enclosed mechanical device.

The navigation system 202 assists in performing a navigated or guided procedure. The guided procedure can be, for example, a surgical procedure, a neural procedure, a spinal procedure, and an orthopedic procedure. The navigation system 202 allows a user, such as a surgeon 220, to view on a display 256 a position of the tool assembly 20 in a coordinate system. The coordinate system can be related to an image, such as in an image guided procedure, or can be related to an imageless procedure.

The navigation system 202 can operate as an image-based system or as an imageless system. While operating as an imageless system, the navigation system 202 can register a subject space (generally defined within and near the subject 152) to a graphical display representing an area of the subject 152, rather than to both the subject space and an image space. Image data of the subject 152 need not be acquired at any time, although image data can be acquired to confirm various locations of instruments or anatomical portions of the subject 152. Positions of the subject 152 can be tracked and positions of the tool assembly 20 relative to the subject 152 can be tracked.

While operating as an imageless system, a position of an anatomical structure can be determined relative to the instrument and the positions of the anatomical structure and the instrument can be tracked. For example, a plane of an acetabulum can be determined by touching several points with the tool assembly 20, or selected tracked tool with at least one of the tracking devices 30. As another example, a position of a femur can be determined in a similar manner. The position of the tool assembly 20 and the anatomical structure can be shown on a display with icons or graphics. The display, however, may not show actual image data captured of the subject 152. Other data can be provided, such as atlas data or morphed atlas data. The atlas data can be image data that is generated or generalized from the subject 152. For example, a brain atlas can be generated based on detail analysis of image data of a brain of a patient. Operation of the navigation system 202 as an image based system is further described below.

Although the navigation system 202 is described as acquiring image data using an imaging device 230, other data may be acquired and/or used, such as patient and non-patient specific data. The imaging device 230 acquires pre-, intra-, or post-operative image data and/or real-time image data of a subject 152. The imaging device 230 can be, for example, a fluoroscopic x-ray imaging device that may be configured as a C-arm having an x-ray source 232 and an x-ray receiving device 234. Other imaging devices may be included and mounted on the imaging device 230. Calibration and tracking targets and radiation sensors may be included with the imaging system 230.

The navigation system 202 may further include an imaging device controller 236. The imaging device controller 236 controls the imaging device 230 to (i) capture x-ray images received at the x-ray receiving section 234, and (ii) store the x-ray images. The imaging device controller 236 may be separate from the imaging device 230 and/or control the rotation of the imaging device 230. For example, the imaging device 28 can move in selected directions around the patient 152. Also, the imaging device may include an O-arm® imaging device as sold by Medtronic, Inc., having a place of business in Minnesota.

Further, an imager tracking device 240 may be included to track a position of selected portions of the imaging device 230 to identify the position of the imaging device 230 relative to the subject 152 while acquiring the image data to assist in registration. The image data can then be forwarded from the imaging device controller 236 to a processing module of a navigation computer 250 wirelessly or via a link 252. The navigation computer 250 can include a processing module that is configured to execute instructions to perform a procedure.

A work station 254 can include the navigation computer 250, a navigation display 256, a user interface 258, and an accessible memory system 260. The image data may be transmitted from the controller 236 to the work station 254 or to a tracking system 204. The workstation 254 may be a portable computer, such as a laptop computer or a tablet computer. The navigation computer 250 including the computer module may include a general purpose processor that executes instructions for navigating the tool assembly 20 and/or may include an application specific circuit. The tracking system 204, as discussed further herein, may include a coil array controller (CAC) 260 having a navigation device interface (NDI) 262.

While the imaging device 230 is shown in FIG. 1, any other alternative 2D, 3D or 3D imaging acquired over time to include four dimensions, imaging modality may also be used. Examples include those discussed above, and further any imaging device, such as isocentric fluoroscopy, bi-plane fluoroscopy, ultrasound, computed tomography (CT), multi-slice computed tomography (MSCT), T1 weighted magnetic resonance imaging (MRI), T2 weighted MRI, high frequency ultrasound (HIFU), positron emission tomography (PET), optical coherence tomography (OCT), intra-vascular ultrasound (IVUS), ultrasound, intra-operative, computed tomography (CT), single photo emission computed tomography (SPECT), and/or planar gamma scintigraphy (PGS) imaging devices may be used. Any of these imaging devices may be used to acquire pre- or post-operative and/or real-time images or image data of the subject 152. The images may also be obtained and displayed, generally, in two or three dimensions. In more advanced forms, 3D surface rendering regions are achieved of the subject, which may be rendered or changed in time (fourth dimension). The 3D surface rendering regions may be achieved by incorporating subject data or other data from an atlas or anatomical model map or from pre-operative image data captured by MRI, CT, or echocardiography modalities. Image data sets from hybrid modalities, such as positron emission tomography (PET) combined with CT, or single photon emission computer tomography (SPECT) combined with CT, can also provide functional image data superimposed onto anatomical data to be used to reach target sites within the subject 152.

The navigation system 202 further includes the tracking system 204. The tracking system 204 includes a localizer 264, which may also be referred to as a transmit coil array (TCA), a tracking array, or a transmit coil assembly. The TCA 264 includes one or more coil groups or sets 266, as discussed further herein, that can transmit or receive a signal and/or generate a field. The tracking system 204 may include the CAC 260, the localizer 264, and the instrument tracking device 30 of the tool assembly 20. It is understood that the tracked portion may be generally referred to as an instrument and that the tracking device may be generally referred to as an instrument tracking device. The tracking system may also track a dynamic reference frame (DRF) 270. All tracked portions are connected to the CAC 260 via the NDI 262. The CAC 260 and the NDI 262 can be provided in a CAC/NDI container 272. The NDI 262 may have communication ports that communicate with the localizer 264, the instrument tracking device 30 and/or the DRF 270 wirelessly or via wires.

The coil arrays localizer 264 can transmit signals that are received by the DRF 270 and at least one tracking device 271 (e.g., the instrument tracking device 30). The tracking device 30 can be associated with the tool assembly 20 at a location that is generally positioned within the subject 152 during a procedure. The DRF 270 can then transmit and/or provide signals, from the DRF tracking device 271, based upon the received/sensed signals of the generated fields from the localizer 264 and/or other localizers. It is understood that the tracking system may also be operated in reverse, where the tracking devices 30, 271 transmit a field that is sensed by the TCA 264.

The DRF 270 can be connected to the NDI 262 to forward the information to the CAC 260 and/or the navigation computer 250. The DRF 270 may be fixed to the subject 152 and adjacent to the region where navigation is occurring such that any movement of the subject 152 is detected as relative motion between the localizer 264 and the DRF 270. The DRF 270 can be interconnected with the subject 152. Any relative motion is indicated to the CAC 260, which updates registration correlation and maintains accurate navigation.

In operation, the navigation system 202 creates a map between points in image data or an image space, such as one defined by an image 280 shown on the display 256, and corresponding points in a subject space (e.g., points in an anatomy of a patient or in a patient space). After the map is created, the image space and subject space are registered to each other. This includes correlating position (location and orientations) in an image space with corresponding positions in a subject space (or real space). Based on the registration, the navigation system 202 may illustrate an icon 282 (which may include a three-dimensional rendering of the instrument, including the tool assembly 20) at a navigated position of the tool assembly 20 relative to an image of the subject 152 in a super-imposed image. For example, the icon 282 can be illustrated relative to a proposed trajectory and/or a determined anatomical target. The work station 254 alone and/or in combination with the CAC 260 and/or the C-arm controller (or control module) 236 can identify the corresponding point on the pre-acquired image or atlas model relative to the tracked tool assembly 20; and display the position on display 256 and relative to the image 280. This identification is known as navigation or localization. The work station 254, the CAC 260, and the C-arm controller 236 and/or selected portions thereof can be incorporated into a single system or implemented as a single processor or control module.

To register the subject 152 to the image 280, the user 220 may use point registration by selecting and storing particular points from the pre-acquired images and then touching the corresponding points on the subject 152 with a pointer probe or any appropriate tracked device. The navigation system 202 analyzes the relationship between the two sets of points that are selected and computes a match, which allows for a correlation of every point in the image data or image space with its corresponding point on the subject 152 or the subject space.

The points that are selected to perform registration or form a map are the fiducial markers, such as anatomical or artificial landmarks. Again, the fiducial markers are identifiable on the images and identifiable and accessible on the subject 152. The fiducial markers can be artificial landmarks that are positioned on the subject 152 or anatomical landmarks that can be easily identified in the image data.

The navigation system 202 may also perform registration using anatomic surface information or path information (referred to as auto-registration). The navigation system 202 may also perform 2D to 3D registration by utilizing the acquired 2D images to register 3D volume images by use of contour algorithms, point algorithms or density comparison algorithms.

In order to maintain registration accuracy, the navigation system 202 tracks the position of the subject 152 during registration and navigation with the DRF 270. This is because the subject 152, DRF 270, and localizer 264 may all move during the procedure. Alternatively the subject 152 may be held immobile once the registration has occurred, such as with a head holder. Therefore, if the navigation system 202 does not track the position of the subject 152 or an area of an anatomy of the subject 152, any subject movement after registration would result in inaccurate navigation within the corresponding image. The DRF 270 allows the tracking system 204 to track the anatomy and can be used during registration. Because the DRF 270 is rigidly fixed to the subject 152, any movement of the anatomy or the localizer 264 is detected as the relative motion between the localizer 264 and the DRF 270. This relative motion is communicated to the CAC 260 and/or the processor 250, via the NDI 262, which updates the registration correlation to thereby maintain accurate navigation.

The tracking system 204 can position the localizer 264 adjacent to the patient space to generate an EM field (referred to as a navigation field). Because points in the navigation field or patient space is associated with a unique field strength and direction, the tracking system 204 can determine the position (which can include location and orientation) of the tool assembly 20 by measuring the field strength and direction or components of the EM field at the tracking device 30. The DRF 270 is fixed to the subject 152 to identify the location of the subject 152 in the navigation field. The tracking system 204 continuously determines the relative position of the DRF 270 and the tool assembly 20 during localization and relates this spatial information to subject registration data. This enables image guidance of the tool assembly 20 within and/or relative to the subject 152.

To obtain a maximum accuracy it can be selected to fix the DRF 270 in each of at least six degrees of freedom. Thus, the DRF 270 or any tracking device, such as the tracking device 30, can be fixed relative to axial motion X, translational motion Y, rotational motion Z, yaw, pitch, and roll relative to a portion of the subject 152 to which the DRF 270 is attached. Any appropriate coordinate system can be used to describe the various degrees of freedom. Fixing the DRF 270 relative to the subject 152 in this manner can assist in maintaining maximum accuracy of the navigation system 202.

The tool assembly 20 can include the stylet, drill, etc., as discussed above. Thus, reference to the tool assembly 20 is not intended to limit the instrument that may be tracked and navigated. With reference to any appropriate navigated instrument, it may include the tracking device 30 that may include the power source 66 and generator 70. The power supply may be charged, as discussed above, and the tool may be tracked with the navigation system as discussed above.

Figure 2:
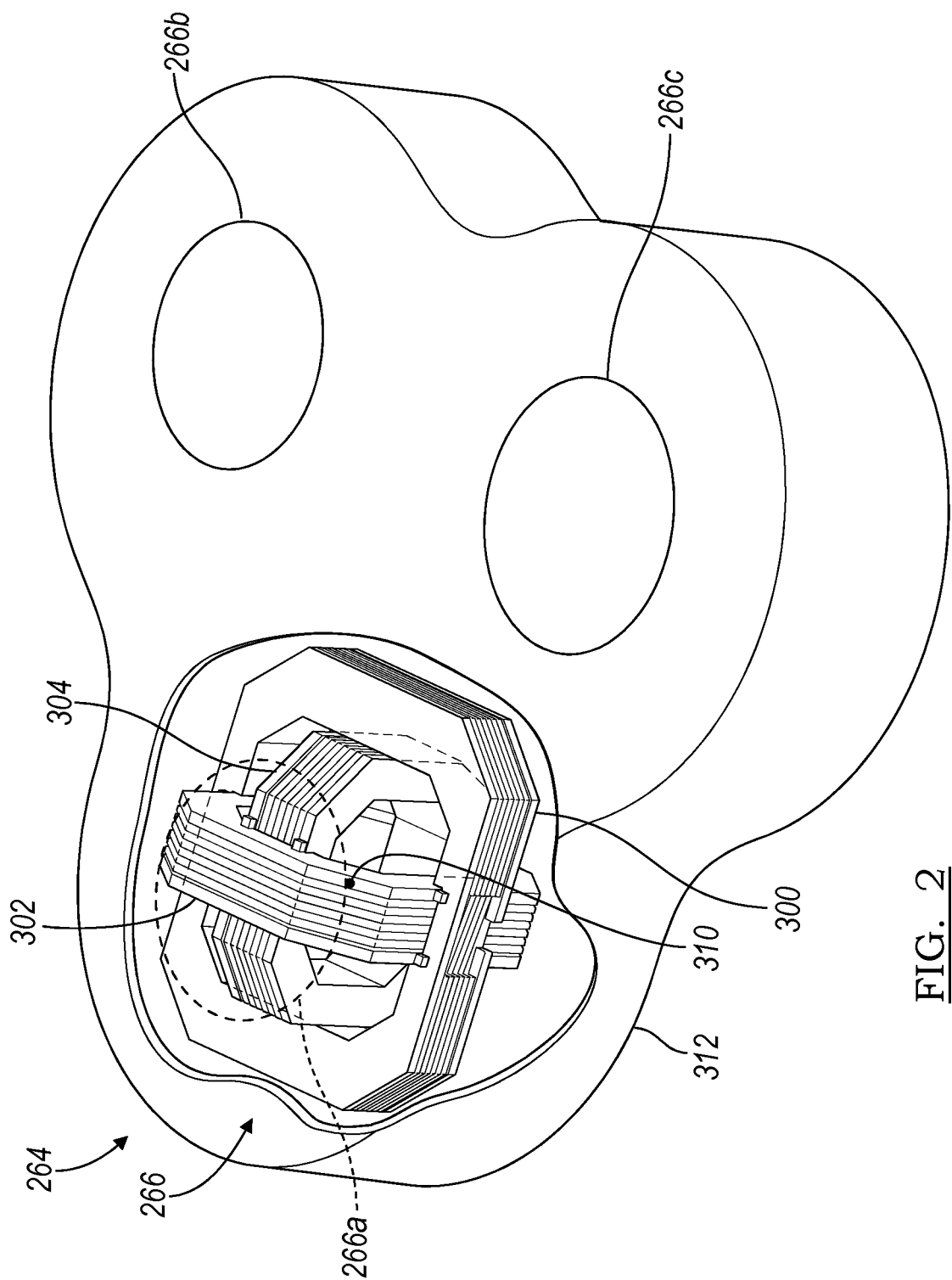
FIG. 2 is a detail transparent view of a transmitter coil array, according to various embodiments.
Figure 4:
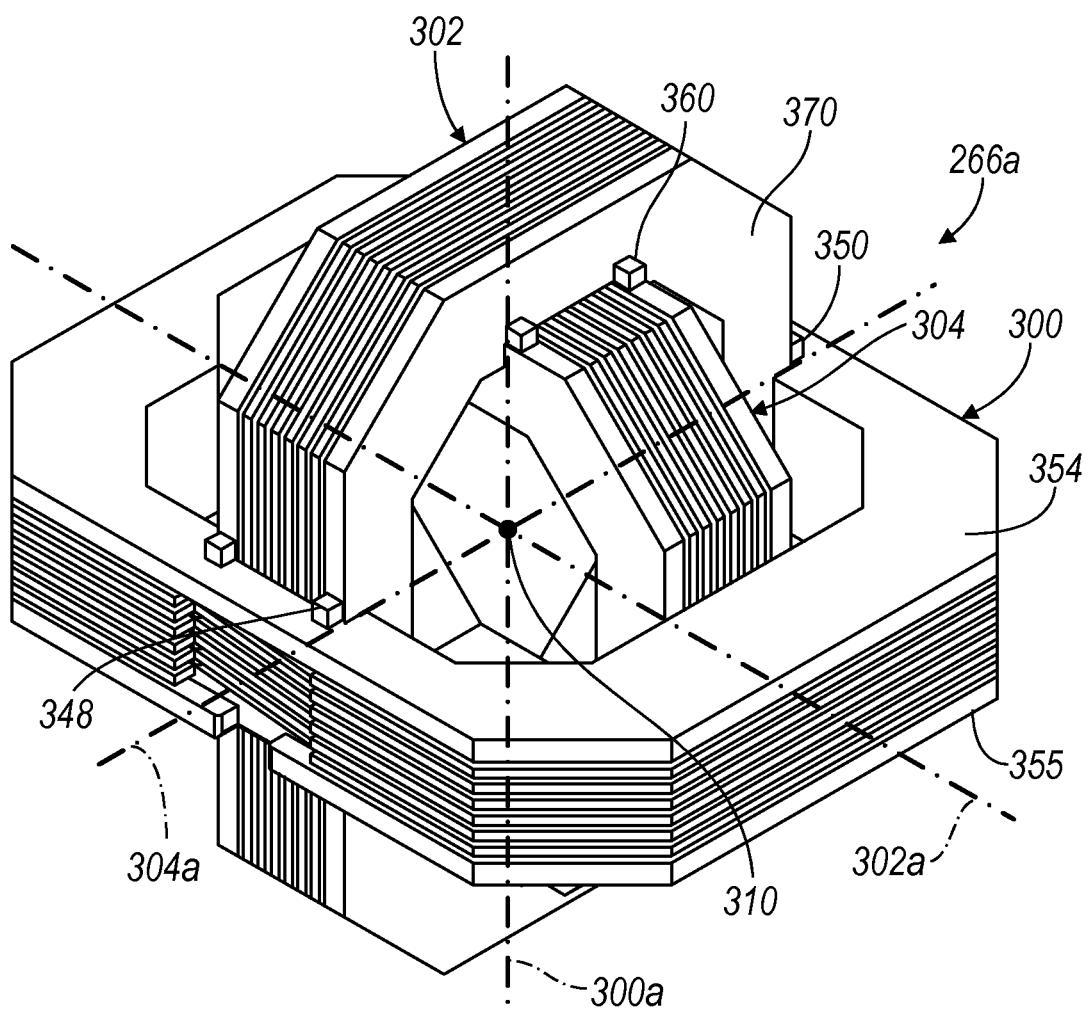
FIG. 4 is an assembled view of a coil group, according to various embodiments.

The navigation system 202, as discussed above, includes the TCA 264 that may have one or more coil sets or groups 266. With continuing reference to FIG. 1, and additional reference to FIG. 2, the TCA 264 may include the coil groups 266 formed of various coil elements or portions, including a first large coil portion 300, a second medium coil portion 302, and a third small coil portion 304. Each of the coil portions 300-304 may be manufactured separately and assembled together, and the size designation or number designation is only for ease of the current discussion, unless specifically noted otherwise. The coil portions 300-304 may be positioned to generate a field of substantially orthogonal to one another, but around a common center 310. As disclosed above, however, a common center is not required, even when the individual coils are formed on jigs, as discussed herein. In other words, as illustrated in FIGS. 2 and 4, each of the coils has a respective axis 300*a*-304*a* around which the coil is wound. All of these axes intersect at only one point, which is the center 310. Further, the coil groups 266 can include a first coil group 266A, a second coil group 266B, and a third coil group 266C.

It is understood, however, that the TCA or localizer 264 can include any appropriate number of the coil groups such as four of the coil groups 266. Additional coil groups may be used for redundancy and accuracy of tracking. Further, it is understood that each of the coil groups need not include the three coil elements 300-304, but may generally include three to provide a selected degree of information, such as including six-degree of freedom information, relating to or for determining the location of the tracking device 30 associated with the instrument 20. Further, it is understood that the TCA 264 need not be provided as a separate or movable portion or member, such as within a casing 312, but might be formed as a portion of a patient support 314 or other appropriate portion positioned relative to the subject 152. Nevertheless, for the following discussion, the TCA 264 is exemplarily illustrated as a movable unit including three of the coil groups 266, where each of the coil groups includes three coil elements or portions 300-304.

It is understood that each of the coil groups, 266A-266C can include three individual coil elements for generating a field relative to the subject 152 or any appropriate volume. As noted above, the field can generally define or form a navigation space that allows for the tracking device 30 to be tracked within the navigation volume of space. This volume of space can include a subject space, such as a selected space of the subject 152 including within the skull 150 of the subject 152. The subject space can be generally positioned within the navigation space, and the navigation space can then be registered to the image space, again as noted above. This allows for registration of the navigation space to the image space and allows for display of the icon or representation of the instrument 282 relative to the image 280 of the subject 152 on the display device 256.

The coil groups, such as the group 266A, can include the three coil elements 300, 302, and 304. Each of the coil elements can generally include a jig or coil form, including a large coil form 320 for the large coil element 300. A medium coil jig or form 322 for the medium coil element 302, and a small coil form or jig 324 for the small coil portion 304. Each of the jigs 320-324 may be formed according to various manufacturing techniques, such as casting, additive manufacturing, rapid prototyping, 3-D printing, injection molding, machining, or the like. As an example, the jigs may be formed using, for example, stereolithography. As another example, alumina ceramic may be printed using a stereolithography process or a cast process to form one or more of the jigs. The jigs may be formed of selected materials, including, nylon, polyvinylchloride, polycarbonate, polyester, polysulphone, polyphenylenesulphone, polyetheretherketone, polyphenylene, sulphide, polyetherimide, polyamide-imide, and/or polybenzimidazole. The materials of the jigs may have coefficients of thermal expansion that are less than predetermined values. Various manufacturing techniques and materials can include that disclosed at U.S. Patent Application Publication 2014/0323852, incorporated herein by reference.

The jigs 320-324 can be formed to include various geometries and configurations such as annular, circular, square, octagonal, hexagonal, or other appropriate configurations. According to various embodiments, the jigs 320-324 are generally inert and/or invisible to any EM field generated with a coil formed on the jigs 320-324. Further, as illustrated herein, each of the jigs may have an internal surface that forms a hollow or void. Thus, each of the coil portions 300-304 generally include an air core or equivalent thereto. In other words, the jig portion on which the coils are wound does not affect the field produced by the coil, even if the coil remains on the jig during use. The coil generally includes a wire, as discussed herein, which is wound on the respective jig 320-324. A current driven through the wire generates the EM field. The wire is generally wound on an exterior surface of the respective jig 320-324.

Generally, as illustrated in FIG. 3, each of the coil jigs 320-324 can be generally octagonal, including non-regular sides. The non-regular octagons can include eight sides, where each of the sides includes a different length or, as illustrated in FIG. 3, each of the coil jigs 320-324 can include four short generally equally length sides and four other sides. In the various jigs, the four remaining sides of the octagon may have two sides of the same length and two more of a same length, but different than the other two. In other words, each of the jigs may be generally square with faceted or straight corners. The octagonal shape assists in forming the coil of wire around the jig, as discussed herein. Further, the octagonal shape assists in modeling the field formed by the coil formed on the respective jig 320-324. For example, the faceted corners can allow the wire to wrap more evenly and precisely, such as following the shape of the jig more closely. Complex shapes or shapes with sharp edges or corners may not allow the coil to be wrapped as discretely and may affect the shape of the coil, thus making modeling of the field more difficult.

As an example, with reference to the jig 320, it may include four generally equal length short sides 320a, 320b, 320c and 320d. Each of the short sides 320a-320d may be generally the same length. Two medium length sides 320E and 320F may extend between adjacent short sides, such as short side 320a and 320d and 320b and 320c. A final two long sides 320g and 320h may be longer than the two medium length sides 320f and 320e, but the two long sides 320g and 320h may also be at the same length. The jig 320 may further include an exterior surface 354 and an opposed exterior surface 355. Generally, as discussed herein, the coil is formed between the two exterior surfaces 354, 355.

It is understood, however, that the other jigs may be formed in a similar configuration or a different configuration. For example, the small jig 324, may have four short sides of generally equal length or equal length, and four other sides that are longer than the short sides, but also of generally equal length. Nevertheless, each of the jigs 320-324 may include a generally equivalent geometry as illustrated and discussed herein. Further, each of the jigs may include opposed exterior surfaces between which the coil is formed.

The octagonal configuration of the jigs 320-324 may allow for forming a field having a geometry and field strength of a selected shape and configuration. The jigs may be further formed, such as in depth of the main coil channel, diameter, etc. to create a field diversity to assist in identifying a location of the tracking device 30. The octagonal geometry, however, may also allow for ease of repeatability between different production runs of the jigs and/or coil windings (as discussed further herein and above). The field strength can be determined over the navigation volume, but include a field strength variability to allow for precise and/or efficient calculation of the location of the tracking device 30. It is understood that other possible shapes for the jigs 320-324 may form different field shapes and require and/or allow for different field or tracking preciseness.

Figure 3A:
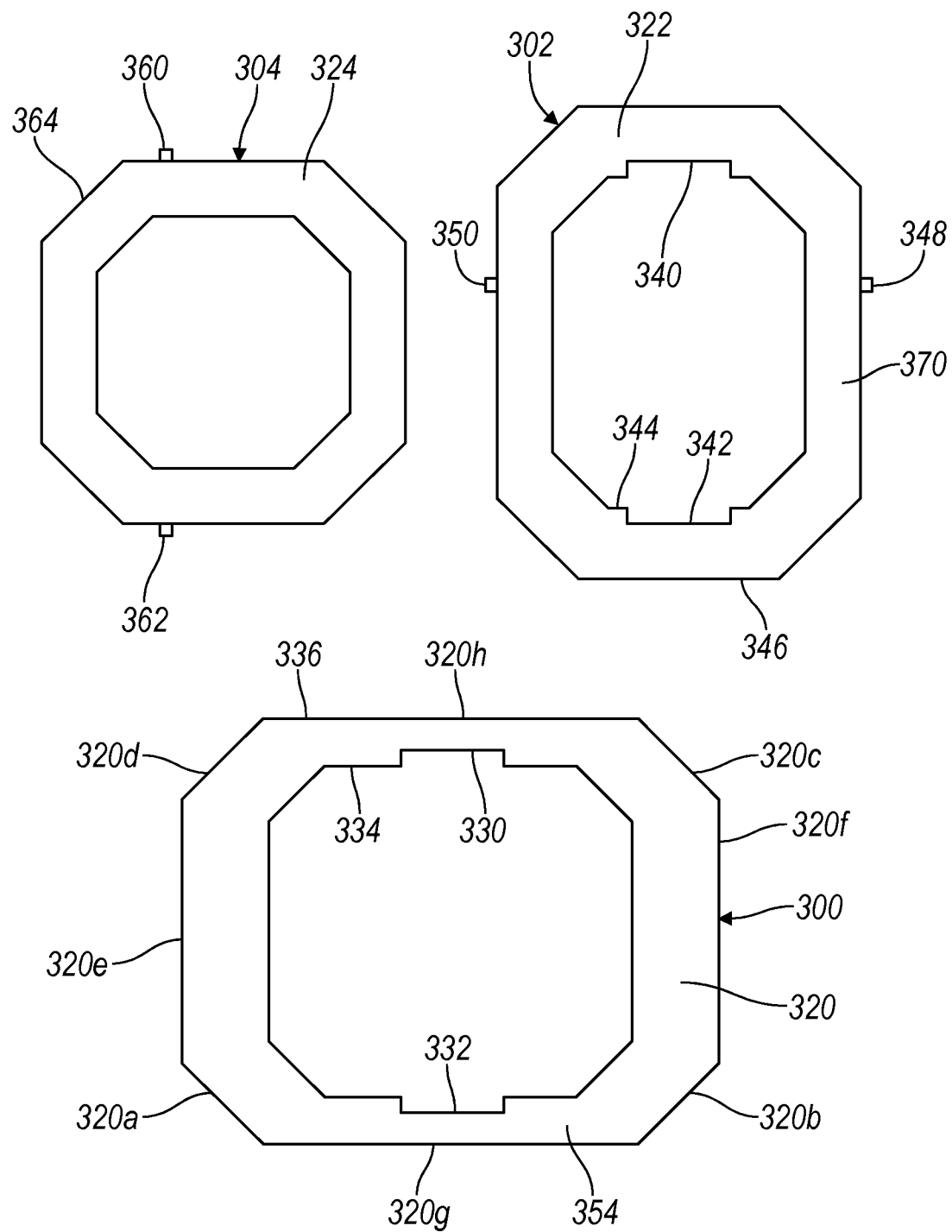
FIG. 3A is an exploded view of a coil group, according to various embodiments.
Figure 3B:
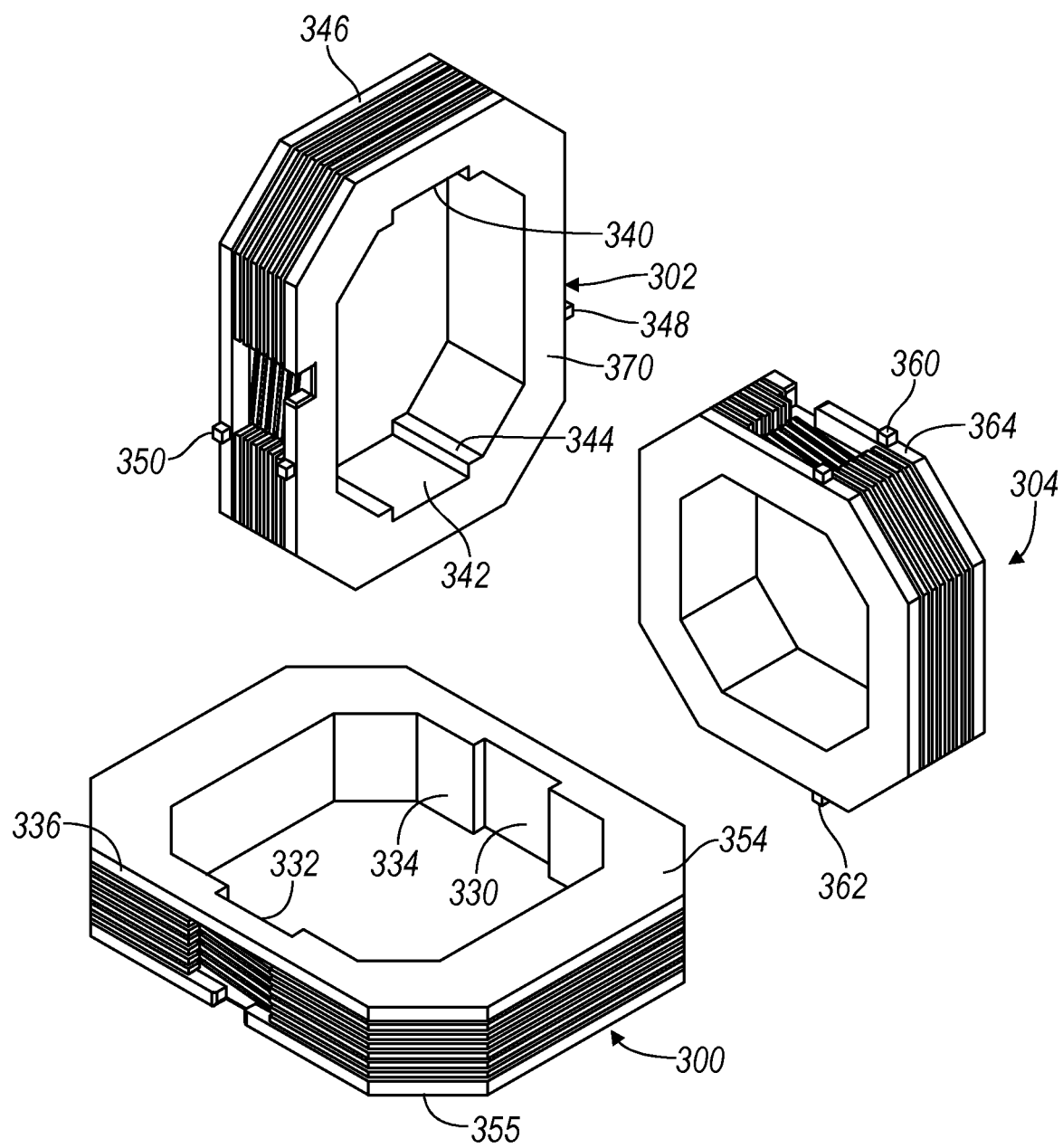
FIG. 3B is an exploded view of a coil group, according to various embodiments.

As illustrated in FIGS. 3A-3B, each of the jigs 320-324 may further include additional geometry besides an external perimeter geometry. For example, as illustrated in FIG. 2, the three coil portions 300-304 will be assembled into a single assembly to form one of the coil groups 266. Therefore, each of the jigs may include portions that assist in assembling the three coil portions 300-304 into the single coil group 266A that includes the common center 310.

The first or large jig 300 may include a first coil portion receiving groove or depression 330 and a second coil receiving portion 332. The grooves 330, 332 can be recesses that are generally opposed to one another and formed in an inner surface 334 and extending towards an outer surface 336 of the jig portion 320. The recesses or grooves 330, 332 can extend a dimension, such as a depth of the jig 320. As discussed further herein, this can allow the other jig members, such as the jig 322 to slide into the respective recesses 330, 332 for assembly of the coil group.

The medium sized jig member 322 may include grooves or recesses, including a first recess 340 and a second recess 342. The recesses can be opposed to one another and formed as depressions in an inner wall or surface 344, where the depression extends towards the outer wall or surface 346. Further, the medium jig member 322 can include one or more stops, such as two stops 348 and 350. The stops 348, 350 can extend from the exterior wall surface 346. As discussed further herein, the stops 348, 350 can engage a surface, such as an upper side surface 354 of the large jig member 320 to assure or assist in achieving a proper (i.e. predetermined and selected) position of the second jig member 322 relative to the first jig member 320. It is understood that additional stops or different formations of the stops 348, 350 can be provided to engage the jig member 320. Further, it is understood that stops 348, 350 need not be required but may be included for assembly ease and/or confirmation. Further, the stops 348, 350 may allow for achieving small or tight tolerances in forming the coil groups.

The third jig member 324 may include stops 360 and 362 similar to the stops 348 and 350 of the second jig member 322. The stops 360, 362 on the third jig member 324 can extend from an exterior surface 364 of the third jig member 324 and could be sized and configured to have selected sides be received within the depression 340 and 342 of the second jig member 322. The stops 360 and 362 can stop or position the third jig member 324 relative to the second jig member 322. Similarly, the stops 348, 350 can stop movement of the second jig member 322 into the first jig member 320, or sides of the second jig member 322 are sized and configured to be received in the depressions 330, 332.

Figure 5A:
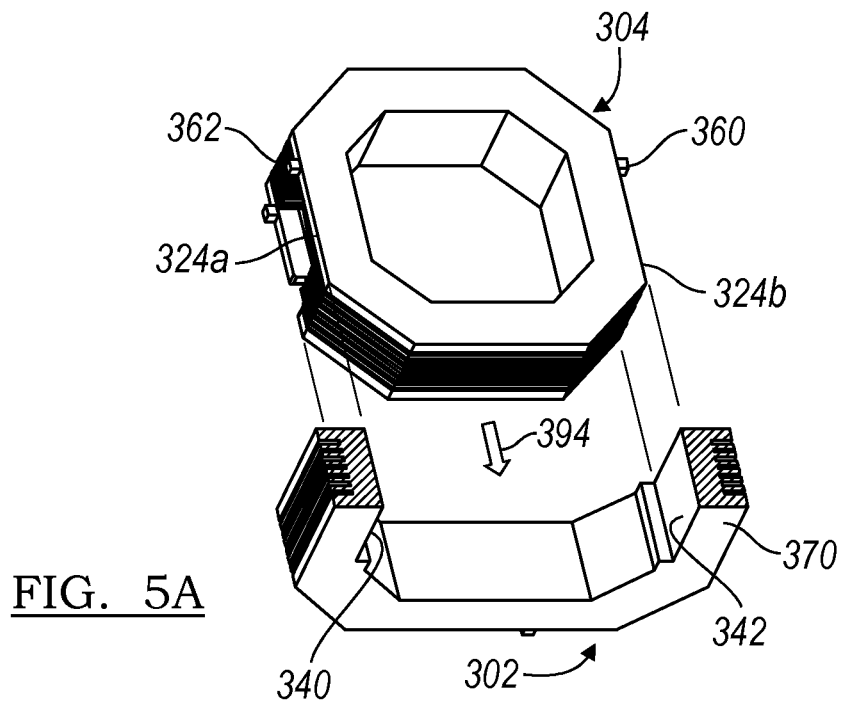
FIG. 5A is a process view of assembling two coil jigs, according to various embodiments.
Figure 5B:
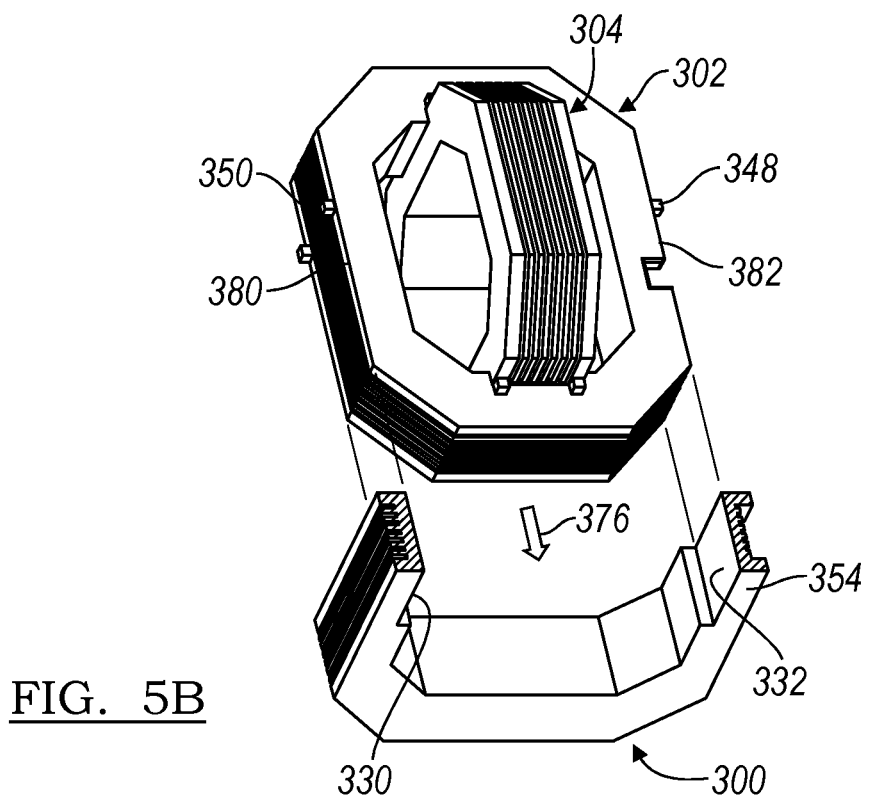
FIG. 5B is a process view of assembling two coil jigs with a third coil jig, according to various embodiments.

With continuing reference to FIGS. 2, 3A, and 3B, and further reference to FIG. 4, the coil group 266a is illustrated in an assembled configuration, but not in the coil array 264. The coil group 266a includes the first jig or coil portion 300 having inserted it therein, the second coil portion 302, having inserted therein the third coil portion 304. As illustrated in FIGS. 5A-5B, the process of assembling the coil portions 300-304 can be sequential to achieve the configuration illustrated in FIG. 4. Nevertheless, as illustrated in FIG. 4, the medium jig 302 may receive the first small jig 304 in the respective grooves 340 and 342. The stops, including stop 360, may engage an external surface 370 of the second jig 322 to stop or position the third jig 304 relative to the second jig 302. Once assembled, the second jig 322 can then be positioned within the respective grooves 330, 332 of the first jig 320. The stops 348, 350 can then engage the surface 354 of the first jig member 300 to position the second jig 322 relative to the first jig 320.

According to various embodiments, therefore, as illustrated in FIG. 5A, the coil group 266 can be assembled form the several coil portions 300-304. The various depressions 330, 332, 340, 342 and stops 348 and 360 can assist in assuring the selected or designed alignment. For example, as noted above the stops 348, 360 may assure the common center 310 of the coil group 266. It is understood, however, as discussed above, that other configurations may be selected and designed. Thus, the depressions and stops may be provided to assure the selected configuration.

In the assembly process, the first jig 324 as the first coil portion 304 can be slid along exterior sidewall surfaces 324A and 324B into the respective grooves or depressions 340 and 342 of the second jig member 322 generally in the direction of the arrow 374. The third jig member 324 can be moved into the depressions 340, 342 until the stops 360 and 362 engage the exterior side surface 370 of the second jig member 322. Once the stops 360 and 362 engage the surface 370, a user may know that the third jig member 324 is properly seated or selectively (e.g. predetermined) positioned relative to the second jig member 322. The second jig 322 and the third jig 324 can be coupled in any appropriate manner such as with an adhesive, a snap fit, or fastener to connect two or more of the jigs 320-324

In various embodiments, it is understood, however, that a controlled mechanism, such as a robotically controlled mechanism, can precisely position the third jig member 324 relative to the second jig member 322 by knowing the three-dimensional location of both of the third jig member 324 and the second jig member 322. Therefore, the physical stops 360 and 362 may not be required, but are illustrated for the current discussion. The assembly may also occur during production and formation of the coil portions 302 and 304 with a machine controlled assembly line.

A coil group sub-assembly is formed, which may include the third jig member 324 being is inserted and assembled into the second jig member 322 to a selected position, such as when the stops 360 and 362 engage the surface 370. The coil group sub-assembly (including the assembled second jig member 322 and third jig member 324) can be inserted into the first jig member 320, as illustrated in FIG. 5B. The assembly of the second jig member 322 and the third jig member 320 can include generally moving the second jig member 322 in the direction of arrow 376. The second jig member 322 is positioned or slides the exterior wall surface 380 and 302 into the respective grooves 330 and 332 of the first jig member 300. The second jig member 302 can be positioned or moved in the direction of arrow 376 until the stop members 348 and 350 engage the surface 354 of the first jig member 320. Again, the stops 348 and 350 can allow for the user or the individual assembling the coil group 266 to determine that the proper position and configuration of the coil members 300-304, including the jigs 320-324, has been achieved.

The stops, including the stops 348, 350, 360, 362 assist in ensuring a proper assembly of the coil group 266. The stops may only allow an assembly in one direction of the coil portion. This can ensure that the field is generated according to generally known or predetermined parameters. Further, as illustrated in the FIGS. 5A-5B, the outer surfaces of the third jig 324 is slid within the inner open portion of the second jig 322 and in the depressions 340, 342 formed on the inner surface therein. The outer surfaces of the second jig 322 are slid within the inner open portion of the first jig 320 and into the depressions 330, 332 formed therein. As noted above, the jigs 320-324 may be held together with selected fixation mechanisms, including adhesives, fasteners, interference or snap fits, etc.

It is understood, however, as noted above, that a robotic mechanism may know the precise position of both the first jig member 320 and the second jig member 322 such that the stops 348 and 350 are not required. Nevertheless, the stops 348 and 350 are disclosed herein for the current discussion. The stops 348 and 350 may provide an indication that the second jig member 322 is positioned in an appropriate location relative to the first jig member 320 and that the assembly is complete such that the common center 310 has been achieved.

With reference to FIGS. 3A-5B, the coil group 266 may be assembled for inclusion in the coil array 264. It is understood that at least three of the coil groups can be assembled as illustrated in FIGS. 3A-5B and included in the coil array 264, as illustrated in FIG. 2. It is further understood, however, that any appropriate number of coil groups need be included in the selected coil array, which may include more than three coil groups 266A-266C or less than three coil groups.

Further, it is understood that the jigs 320-324 allow for a modular creation of each of the three coil portions 300-304 that form the coil group 266. Thus, each of the jigs 320-324 may be wound with conductive material, such as copper wire having a gauge of about 22 AWG to about 32 AWG (including an outer diameter of about 0.65 mm to about 0.2 mm). It is understood, however, that wire of any appropriate gauge may be selected depending up selected field configurations, power, etc. The jigs 320-324 may be individually wound separately and then assembled together to form the final coil group 266, as illustrated in FIGS. 3A-5B. Thus, the formation of the individual coil portions on the respective jigs 320-324 can occur in an appropriate manufacturing technique and step without requiring the formation of all three coils, for forming the coil group 266, substantially simultaneous or a fixed sequential manner.

Figure 6:
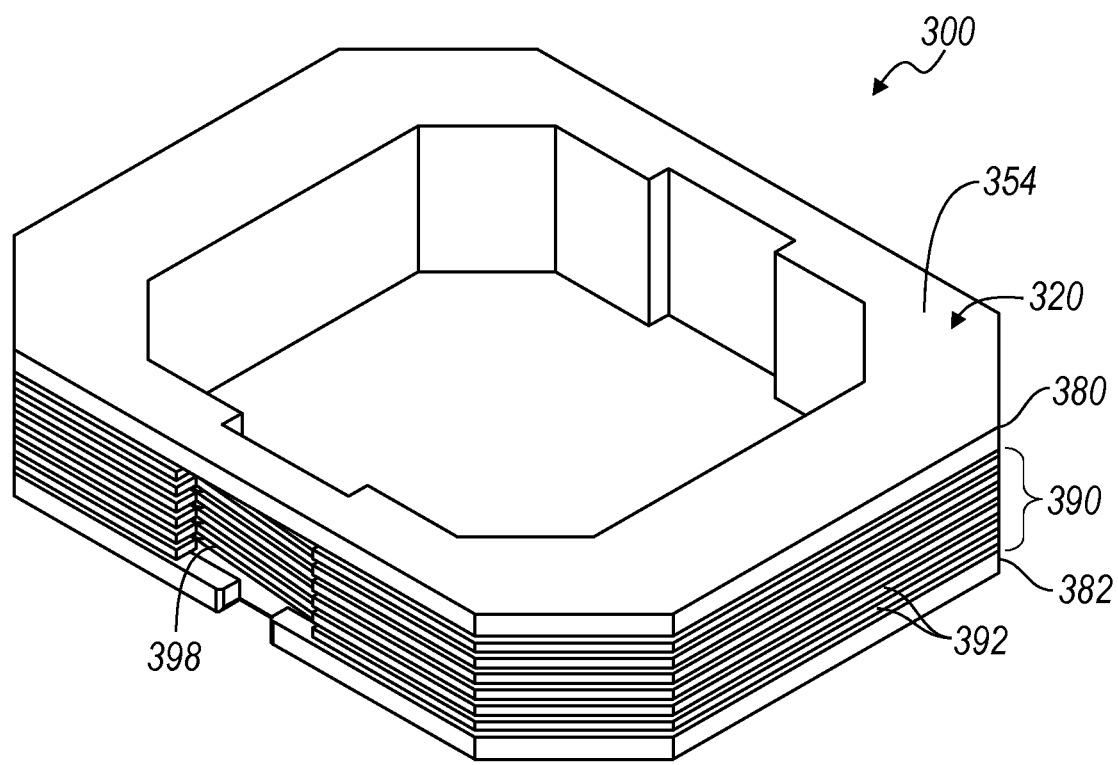
FIG. 6 is a perspective view of a single coil jig, according to various embodiments.
Figure 7A:
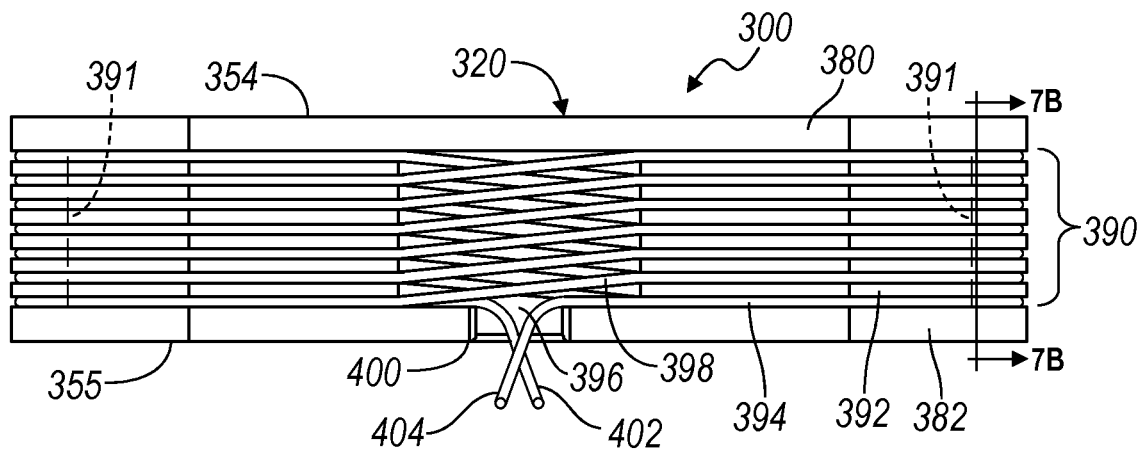
FIG. 7A is a side plan view of a single coil jig, according to various embodiments.
Figure 7B:
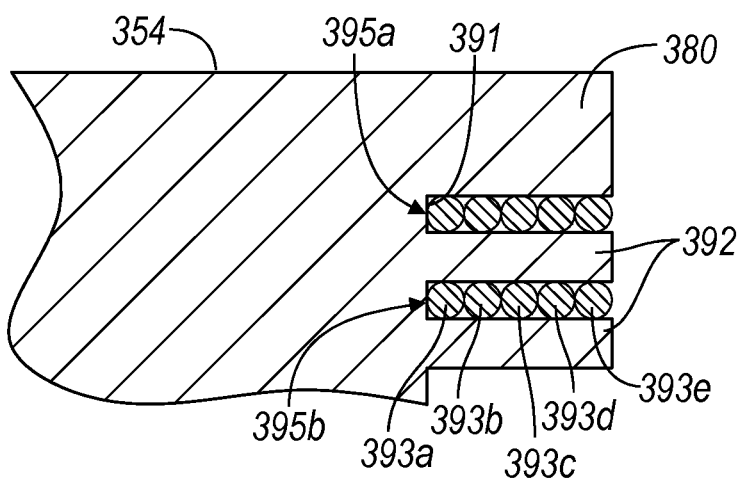
FIG. 7B is a detail cross-sectional view of a wrapped jig of FIG. 7A.

The various coil portions 300-304, as discussed above, can include the coil portion 300 as illustrated in FIGS. 6, 7A, and 7B. As discussed above, the first coil portion 300 can include the jig 320. The jig 320 and the coil of wire placed thereon is discussed here, but it is understood that a similar process and details may be included on any appropriate jig.

The jig 320 can include a first external wall 380 that can form the top surface 354 and a second external wall 382. Between the first external wall 380 and the second external wall 382 can be a main coil or conductive material groove or channel 390. The main groove 390 may also include an external wall 391. As discussed herein, a wire may be wound around the jig 320 and on the external wall 391 to form the coil portion 300. A current driven through the wire will generate the EM field, as discussed above.

According to various embodiments, as illustrated in FIGS. 6, 7A, and 7B, the main groove or channel 390 can include one or more sub-walls or internal walls 392 formed therein. Positioned between the exterior walls 380, 382 and the internal walls 390 can be a coil, including a plurality of windings, of conductive material, such as winds of a wire 393 discussed above. The wire may be wound in sub-grooves 394 formed between each of the sub-walls 392 and the respective sub-walls 392 and external walls 380, 382. The small or sub-grooves 394 can be further at least partially formed or defined by a surface 396 of the jig 320 including a surface grooves 398. The grooves, including the surface grooves 398 and the sub-grooves 394, may allow the windings to be manually wound around the jig 320 in a substantially repeatable manner. Generally, about 5-10, including about 8-10 windings can be formed in each of the sub-grooves 394 and surface grooves 398 around the jig 320. It is understood that more or less windings can be provided within the respective grooves depending upon the field strength selected to be formed by the coil portion 300. Each winding group, such as between the walls 392 may be connected to the other winding groups so that the coil portion 300 forms a single coil. Further, the jig 320 can include an exit spot or portion 400 to allow the leads 402, 404 of the wire formed on the jig 320 for connection to control portions, such as the CAC controller 260. The sub-grooves 394, and surface grooves 398 can allow for ease of repeatability of forming coils on the jig 320.

As illustrated in FIG. 7B, the wire 393 may be wound in a plurality of windings 393a-393e, any appropriate number of windings may be included. Further, a first row of windings 395a (i.e. winding group) may be separated and spaced apart from a second row of windings 395b (i.e. winding group) by one of the walls 392. The two winding groups 395a, 395b may be connected, as noted above. Any appropriate number of the windings groups may be provided on the jig 320 and all may be connected. It is understood, however, as discussed herein, that the several windings need not be so separated from one another. Further, the external walls 380, 382 may be co-extensive or extend beyond the windings, as illustrated in FIG. 7B.

Further, the jig 320, or other jig portions, may include one or more of the surface grooves 398. The surface grooves allow the first winding of each winding portion to be at least partially, and even completely, recessed into the surface of the main groove 390. Thus, as the wire winding moves from one of the sub-grooves 392 to another sub-groove 394 the wire may be first recessed. Successive windings, therefore, may be flatter and smoother through the transition. This surface groove 398, therefore, allows the coil to be smoother, more even, and not include a bump in the transition area. Thus, field created by the coil portion 300 may be more uniform and more repeatable between coil forms.

It is further understood that the jig 320 may be wound in a plurality of manners. As described above, the surface groove 398 may assist in assuring a flat transition area if each successive winding moves to an adjacent sub-groove. It is understood, however, that the coil portion 300 may be formed by completely winding each sub-groove before winding in another adjacent sub-groove. Or each sub-groove may have a selected number of windings, such as two or three, then the next sub-groove, and then the jig may be wound back again.

In providing a substantially repeatable and/or uniform configuration of the coil wire from one manufactured coil portion to another manufactured coil portion, calibration may be performed more efficiently and/or substantially minimized or reduced in time for calibrating the TCA 264. The jigs 320-324, therefore, allow the coil portions 300-304 to be manufactured with tight or small tolerances. As discussed above, the winding of the coil portion 300 with a conductive material can be performed for each of the coil portions including each coil portion for a plurality of the coil groups that may be included in the TCA 264. Accordingly, the illustration of the coil portion 300 in FIGS. 6 and 7 is merely exemplary.

Figure 8:
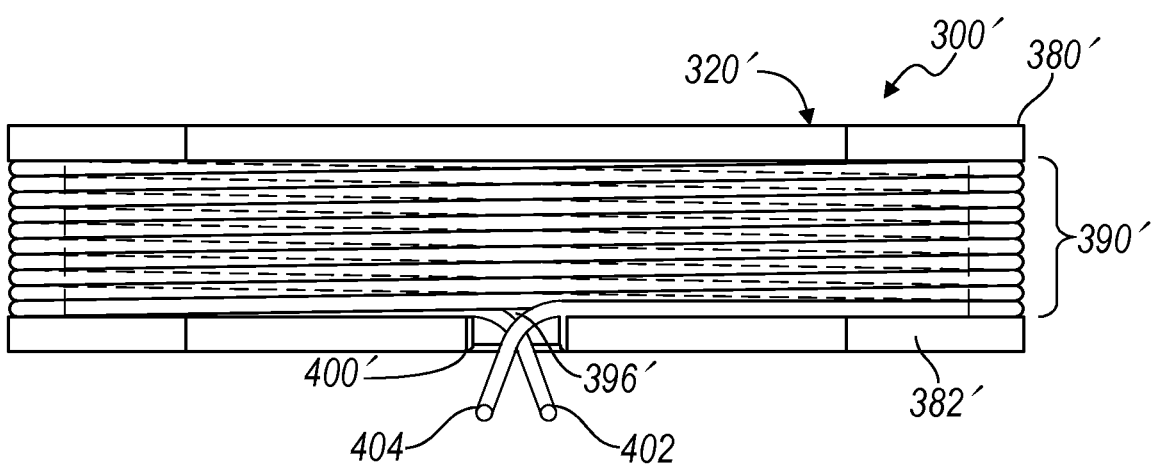
FIG. 8 is a side plan view of a single coil jig, according to various embodiments.

With additional reference to FIG. 8, an alternative configuration of the coil portion 300 as illustrated as coil portion 300'. The coil portion 300' may include portions that are substantially similar to the coil portion 300, including the jig 320 as discussed above. A jig 320', however, of the coil portion 300', may include only the external wall 380' and the external wall 382' while not having any internal walls 392. A plurality of windings of the wire 393 may be sequentially formed on the jig 320', however, using various winding techniques and/or mechanisms. Winding machines such as the Star Winder, sold by Gorman Machine having a place of business in MA, can be programmed to manipulate the jig 320' to neatly and uniformly form windings and layers of coils of the connective material within the main groove 390' without including the internal walls 392.

The main groove 390' can maintain the multiple coils within or on the jig 320' while the winding machine can be programmed to move the conductive material or the jig 320', or both, to form the stacked coils on the jig 320'. The coils may be wrapped on each other or stacked on one another, as illustrated in FIG. 7B without the wall 392. The wire 393 may further include an adhesive coating to assist in maintaining the wound configuration. The windings of the conductive material on the jig 320', however, may be substantially similar as the windings formed on the jig 320 that includes the internal walls 392, but not separated by the walls 392.

The substantially precise and neat winding, e.g. with tight tolerances, of the conductive material on the jig 320' can allow for repeatability between the coil portions manufactured at different times, as discussed above. The repeatability can assist in reducing calibration time and/or eliminating calibration time. As discussed above, the calibration can be calibration after manufacturing to identify the shape of the field and determine variability of the field strength therein for navigation.

According to the various embodiments, including those discussed above, the transmitter coil array 264 of the navigation system 202 may be formed to generate or emit an electromagnetic field to define a navigation space relative to a subject, such as the human subject 152. In providing the plurality of modular jig members 320-324, coil portions 300-304 that form the coil groups 266 can be formed separately and separately assembled according to a selected manufacturing technique and process, including that discussed above. Therefore, forming two or more coils of wire for the TCA 264 substantially simultaneously or during a single processing step need not occur. The various coil portions can be formed separately and then efficiently, as illustrated in FIGS. 5A and 5B, assembled together. The assembly can then be provided in forming the TCA 264 for emitting a field for navigation. This can allow for minimizing manufacturing steps and simply efficiently forming jigs to form single coils.

Moreover, the coils may be manually wound or rewound for various purposes with small tolerances. Although, according to various embodiments, the jigs 320-324 may be formed to allow for substantially automatic or machine winding of the single coil portions, without requiring intricate manipulation of a jig to form the coil group 266, as discussed above. The separate coil portions can be assembled, as discussed above, for forming the coil group 266 and subsequently forming the TCA 264. This can allow a method of forming the first coil portion 300, forming the second coil portion 302, and forming the third coil portion 304, and then assembling the first coil portion 304 into the second coil portion 302 and then assembling the assembly of the first and second coil portions into the third coil portion 300. Such a method allows for a modular construction of the coil group 266 for various purposes.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system for navigating an instrument, comprising:
 a first coil jig having at least a single first coil of conductive material positioned thereon;
 a second coil jig having at least a single second coil of conductive material positioned thereon; and
 a third coil jig having at least a single third coil of conductive material positioned thereon;
 wherein the first coil jig is configured to be assembled with the second coil jig and the second coil jig is configured to be assembled with the third coil jig to form together a coil group having connected together the first coil jig, the second coil jig, and the third coil jig,
 wherein the first coil jig includes (i) a first external wall spaced apart from (ii) a second external wall and a main coil channel defined between the first and second external walls, and
 wherein the main coil channel (i) includes a depth between the first external wall and the second external wall that is configured to have wrapped at least the single first coil of conductive material and (ii) having at least eight surfaces formed between the first and second external walls to create faceted corners to allow at least the single first coil to be wrapped according to selected tolerances about the at least eight surfaces to at least assist in modeling the field formed by at least the single first coil of conductive material formed on the first coil jig.

2. The system of claim 1, wherein the coil group includes a common center for each of the first coil jig, the second coil jig, and the third coil jig.

3. The system of claim 1, wherein the first coil jig, the second coil jig, and the third coil jig are all separate from one another.

4. The system of claim 1,
 wherein the main coil channel includes at least one internal wall that forms at least one sub-groove formed within the at least one of the eight surfaces of the main coil channel, and wherein the sub-groove is configured to receive a first conductive material to form at least the single first coil of conductive material.

5. The system of claim 4, wherein the sub-groove includes a plurality of sub-grooves formed parallel to each other between the first and second external walls.

6. The system of claim 5,
 wherein the second jig includes (i) a third external wall spaced apart from (ii) a fourth external wall and a second main coil channel defined between the third and fourth external walls, wherein the second main coil channel (i) is configured to receive at least the single second coil of conductive material and (ii) having at least eight surfaces formed between the third and fourth external walls to create faceted corners to allow at least the single second coil to be wrapped according to selected tolerances about the at least eight surfaces to at least assist in modeling the field formed by at least the single second coil of conductive material formed on the second jig; and
 wherein the third jig includes (i) a fifth external wall spaced apart from (ii) a sixth external wall and a third main coil channel defined between the fifth and sixth external walls, wherein the third main coil channel (i) is configured to receive at least the single third coil of conductive material and (ii) having at least eight surfaces formed between the fifth and sixth external walls to create faceted corners to allow at least the single third coil to be wrapped according to selected tolerances about the at least eight surfaces to at least assist in modeling the field formed by at least the single third coil of conductive material formed on the third jig.

7. The system of claim 1, wherein each of the first coil jig, the second coil jig, and the third coil jig include an open center;
 wherein the first coil jig is received within a first open center of the second coil jig,
 wherein the second coil jig is received within a second open center of the third coil jig, and
 wherein the second coil jig is received within the second open center of the third coil jig with the first coil jig received within the first hollow center.

8. The system of claim 1, further comprising:
a navigation system including a tracking system having the transmitter coil array; and
a tracking device configured to be tracked with a field generated by the transmitter coil array.

9. The system of claim 8, wherein the coil group includes a plurality of coil groups.

10. The system of claim 1, wherein the first coil jig includes a first stop member extending from an exterior surface of the first coil jig, wherein the first stop member is configured to engage a second exterior surface of the second coil jig in the coil group.

11. The system of claim 1, wherein the first coil jig having at least the single first coil of conductive material positioned thereon includes at least the single first coil of conductive material being wound on the first coil jig,
wherein the second coil jig having at least the single second coil of conductive material positioned thereon includes at least the second first coil of conductive material being wound on the second coil jig, and
wherein the third coil jig having at least the single third coil of conductive material positioned thereon includes at least the single third coil of conductive being is wound on the third coil jig.

12. A system for navigating an instrument, comprising:
a transmitter coil array having a coil group, including wherein the coil group includes:
a first coil portion having a first jig with at least a single first coil of conductive material positioned thereon,
a second coil portion having a second jig having at least a single second coil of conductive material positioned thereon, and
a third coil portion having a third jig having at least a single third coil of conductive material positioned thereon,
wherein the coil group is formed by the first coil jig assembled within the second coil jig, and the second coil jig having the first coil jig assembled therein is assembled with the third coil jig;
a tracking device configured to sense a field generated by the transmitter coil array;
a navigation processor configured to execute instructions to determine a position of the tracking device; and
a display device configured to display a representation at the determined position of the tracking device,
wherein the first coil jig includes (i) a first external wall spaced apart from (ii) a second external wall and a main coil channel defined between the first and second external walls, wherein the main coil channel (i) includes a depth that is configured to have wrapped at least the single first coil of conductive material and (ii) having at least eight surfaces formed between the first and second external walls to create faceted corners to allow at least the single first coil to be wrapped according to selected tolerances about the at least eight surfaces to at least assist in modeling the field formed by at least the single first coil of conductive material formed on the first coil jig.

13. The system of claim 12, further comprising:
an instrument associated with the tracking device, wherein the representation includes an icon displayed with the display device.

14. The system of claim 12,
wherein the second jig includes (i) a third external wall spaced apart from (ii) a fourth external wall and a second main coil channel defined between the third and fourth external walls, wherein the second main coil channel (i) is configured to receive at least the single second coil of conductive material and (ii) having at least eight surfaces formed between the third and fourth external walls to create faceted corners to allow at least the single second coil to be wrapped according to selected tolerances about the at least eight surfaces to at least assist in modeling the field formed by at least the single second coil of conductive material formed on the second jig, and
wherein the third jig includes (i) a fifth external wall spaced apart from (ii) a sixth external wall and a third main coil channel defined between the fifth and sixth external walls, wherein the third main coil channel (i) is configured to receive at least the single third coil of conductive material and (ii) having at least eight surfaces formed between the fifth and sixth external walls to create faceted corners to allow at least the single third coil to be wrapped according to selected tolerances about the at least eight surfaces to at least assist in modeling the field formed by at least the single third coil of conductive material formed on the third jig.

15. The system of claim 14, wherein the third jig includes an open center formed by an internal surface, and
wherein the third jig further includes at least one depression formed within the internal surface to operably engage the second jig in the coil group.

16. The system of claim 15, wherein the second jig includes a stop portion to limit movement of the second jig relative to the third jig.

17. A method of forming a localizer for navigating an instrument with a system, comprising:
forming a coil group by:
positioning at least a single first coil of conductive material on a first coil jig,
wherein the first coil jig includes (i) a first external wall spaced apart from (ii) a second external wall and a first main coil channel defined between the first external wall and the second external wall, and
wherein the first main coil channel (i) includes a depth between the first external wall and the second external wall that is configured to have wrapped therein at least the single first coil of conductive material and (ii) having at least eight surfaces formed between the first and second external walls to create faceted corners to allow at least the single first coil to be wrapped according to selected tolerances about the at least eight surfaces to at least assist in modeling the field formed by at least the single first coil of conductive material formed on the first coil jig;
positioning at least a single second coil of conductive material on a second coil jig;
positioning at least a single third coil of conductive material on a third coil jig;
assembling together the first coil jig, the second coil jig, and the third coil jig.

18. The method of claim 17, further comprising:
generating a field with the coil group.

19. The method of claim 18, further comprising:
sensing the generated field with a tracking device.

20. The method of claim 17, further comprising:
sensing a field with the coil group generated with a tracking device.

21. The method of claim 17, wherein assembling together the first coil jig, the second coil jig, and the third coil jig includes placing the first coil jig and the second coil jig within the third coil jig.

22. The method of claim 21, wherein assembling together the first coil jig, the second coil jig, and the third coil jig includes:

forming a sub-assembly by assembling the first coil jig within an opening formed by the second coil jig, and assembling the sub-assembly of the first coil jig and the second coil jig within an opening formed by the third coil jig;

wherein the second coil jig includes (i) a third external wall spaced apart from (ii) a fourth external wall and a second main coil channel defined between the third and fourth external walls, wherein the second main coil channel (i) is configured to receive at least the single second coil of conductive material and (ii) having at least eight surfaces formed between the third and fourth external walls to create faceted corners to allow at least the single second coil to be wrapped according to selected tolerances about at least the eight surfaces to at least assist in modeling the field formed by at least the single second coil of conductive material formed on the second coil jig; and wherein the third coil jig includes (i) a fifth external wall spaced apart from (ii) a sixth external wall and a third main coil channel defined between the fifth and sixth external walls, wherein the third main coil channel (i) is configured to receive at least the single third coil of conductive material and (ii) having at least eight surfaces formed between the fifth and sixth external walls to create faceted corners to allow at least the single third coil to be wrapped according to selected tolerances about the at least eight surfaces to at least assist in modeling the field formed by at least the third single coil of conductive material formed on the third coil jig.

* * * * *

UNITED STATES PATENT AND TRADEMARK OFFICE
CERTIFICATE OF CORRECTION

PATENT NO. : 11,096,605 B2
APPLICATION NO. : 14/673994
DATED : August 24, 2021
INVENTOR(S) : Andrew Wald et al.

It is certified that error appears in the above-identified patent and that said Letters Patent is hereby corrected as shown below:

In the Specification

Column 5, Line 16, delete "28" and insert --230-- therefor

Column 11, Line 25, delete "302" and insert --322-- therefor

Column 11, Line 28, delete "304" and insert --324-- therefor

Column 11, Line 29, delete "302." and insert --322.-- therefor

Column 11, Line 32, delete "300" and insert --320-- therefor

Column 11, Line 44, delete "324" and insert --320-- therefor

Column 11, Line 45, delete "304" and insert --300-- therefor

Column 12, Line 9, delete "320" and insert --324-- therefor

Column 12, Line 13, delete "300." and insert --320.-- therefor

Column 12, Line 13, delete "302" and insert --322-- therefor

Column 13, Line 64, delete "392" and insert --394-- therefor

Column 15, Line 25, delete "304" and insert --300-- therefor

Column 15, Line 28, delete "300." and insert --304.-- therefor

Signed and Sealed this
Thirty-first Day of May, 2022

Katherine Kelly Vidal
*Director of the United States Patent and Trademark Office*